US00PP20799P2

(12) United States Plant Patent
Stewart

(10) Patent No.: US PP20,799 P2
(45) Date of Patent: Mar. 2, 2010

(54) *ANIGOZANTHOS* HYBRID PLANT NAMED 'RAMBORAMP'

(50) Latin Name: ***Anigozanthos* hybrid**
Varietal Denomination: Ramboramp

(75) Inventor: Ian Angus Stewart, Somersby (AU)

(73) Assignee: Ramm Botanicals Holdings Pty., Ltd., Tuggerah, NSW (AU)

( * ) Notice: Subject to any disclaimer, the term of this patent is extended or adjusted under 35 U.S.C. 154(b) by 0 days.

(21) Appl. No.: 12/315,905

(22) Filed: Dec. 8, 2008

(51) Int. Cl.
*A01H 5/00* (2006.01)

(52) U.S. Cl. ..... Plt./362

(58) Field of Classification Search ..... Plt./362
See application file for complete search history.

(56) References Cited

OTHER PUBLICATIONS

Australian Plant Breeder's Rights Application No. 2008/121 filed Apr. 30, 2008 http://pbr.ipaustralia.plantbreeders.gov.au/ Plant material first became available to the public on Dec. 10, 2007 in the form of an Australian sale.

*Primary Examiner*—Susan B McCormick Ewoldt
(74) *Attorney, Agent, or Firm*—Audrey Charles

(57) ABSTRACT

'Ramboramp' is a distinctive variety of *Anigozanthos* hybrid which is characterized by the combination of its medium to tall plant height, long flowering season, profuse flowering, large flower size and orange-red colored flowers.

1 Drawing Sheet

Latin name of the genus and species: *Anigozanthos* hybrid.
Variety denomination: 'Ramboramp'.

BACKGROUND OF THE INVENTION

The present invention relates to a new and distinct perennial variety of *Anigozanthos* hybrid, which has been given the variety denomination of 'Ramboramp'. Its market class is that of an ornamental plant. 'Ramboramp' is intended for use in landscaping and as a decorative plant.

The *Anigozanthos* hybrid variety 'Ramboramp' was the result of a seedling selection of an unnamed *Anigozanthos* hybrid believed to be *Anigozanthos humilis*×*Anigozanthos flavidus* in 2006 in Tuggerah, New South Wales, Australia. 'Ramboramp' was identified as a single seedling from a group of seedlings planted to a landscape from discarded progeny from a breeding program conducted in 2002 at Tuggerah, New South Wales, Australia. 'Ramboramp' was observed to have desirable traits including strong performance in the landscape, long flowering season, large flower size and tolerance to typical diseases of *Anigozanthos*. The inventive variety was finally selected in July 2006 based on its unique traits. 'Ramboramp' was isolated and subsequently propagated in vitro during 2006 through 2008. Resultant plants were tested in 14 cm pots and in ground during 2007.

Asexual reproduction of the new cultivar by in vitro propagation of micro-plants since 2007 in Tuggerah, New South Wales, Australia has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Ramboramp' as a new and distinct cultivar of *Anigozanthos* hybrid plant:

1. Medium to tall plant height;
2. Long flowering season;

3. Profuse flowering;
4. Large flower size; and
5. Orange-red colored flowers.

Plants of the new cultivar differ from plants of the parent primarily in perianth tube size and length of flowering season. 'Ramboramp' has a long and broad perianth tube creating a large flower size whereas the parent has a smaller perianth tube length and width creating a medium-sized flower. 'Ramboramp' has a long, almost continuous flowering season whereas the parent has a shorter flowering season from late winter to summer. The combination of large flower size with a long almost continuous flowering season, medium to tall plant height, profuse flowering, a orange-red colored flower and tolerance to typical diseases of *Anigozanthos* makes 'Ramboramp' a desirable ornamental plant suited for mass production for pot and landscape use.

Of the many commercially available *Anigozanthos* cultivars, the most similar in comparison to the new cultivar is the cultivar 'Amber Velvet', U.S. Plant Pat. No. 18,999.

However, in side by side comparisons, conducted in Tuggerah, New South Wales, Australia plants of the new cultivar differ from plants of 'Amber Velvet' in at least the following characteristics:

1. 'Ramboramp' has a predominantly orange-red colored perianth tube whereas 'Amber Velvet' has a predominantly orange perianth tube color;
2. 'Ramboramp' has secondary inflorescence ramification whereas 'Amber Velvet' has tertiary inflorescence ramification;
3. 'Ramboramp' has a long almost continuous flowering season whereas 'Amber Velvet' a shorter flowering season from late winter to summer;
4. 'Ramboramp' has a broad and long perianth size whereas 'Amber Velvet' has a medium perianth size, and
5. 'Ramboramp' has a weak perianth lobe reflexing whereas 'Amber Velvet' has strong perianth lobe reflexing.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Ramboramp'.

DETAILED BOTANICAL DESCRIPTION

Figure 1:
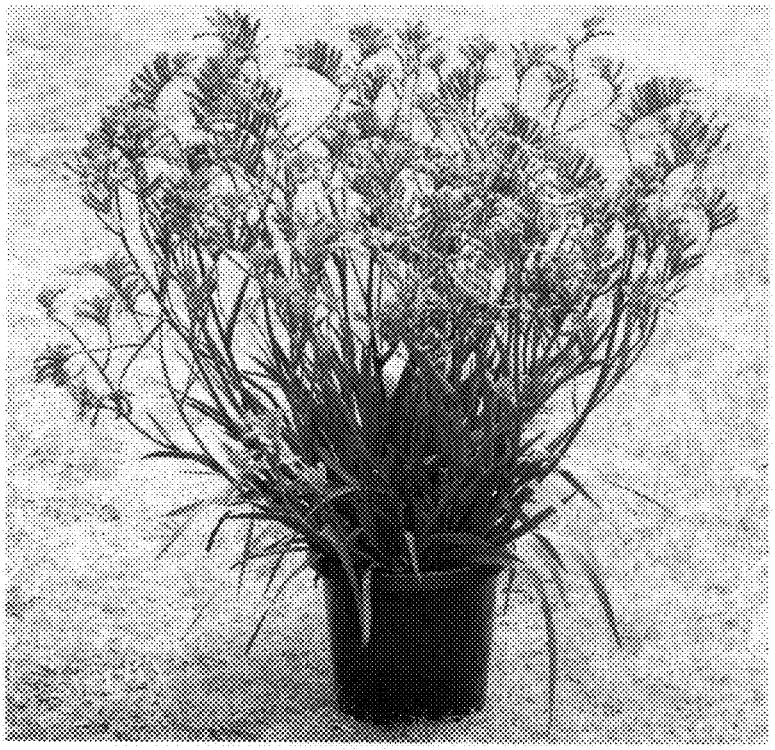
FIG. 1 illustrates a 'Ramboramp' plant in a 30 cm pot grown for approximately 26 weeks in a greenhouse environment.
Figure 2:
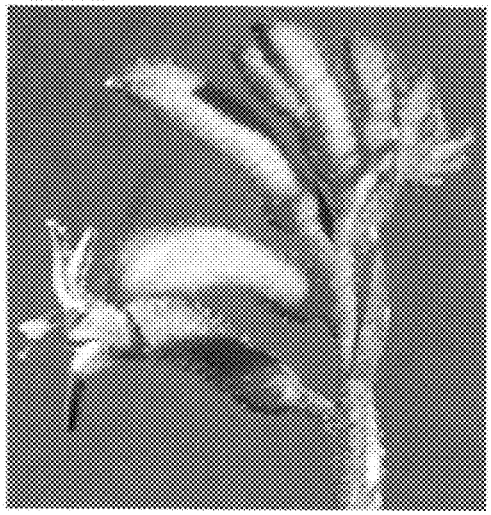
FIG. 2 illustrates a 'Ramboramp' inflorescence branching pattern.
Figure 3:
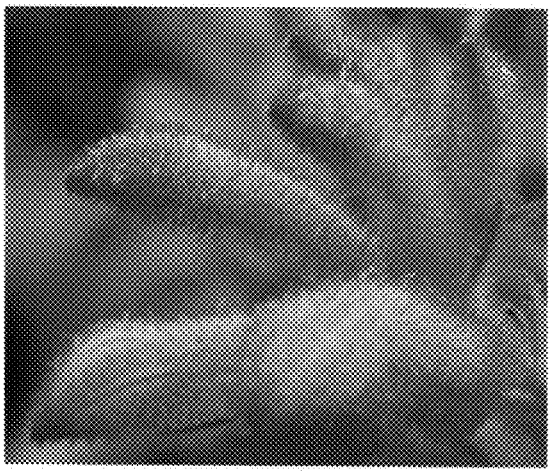
FIG. 3 illustrates 'Ramboramp' flowers within the inflorescence showing flower and hair detail.

The following is a detailed botanical description of a new and distinct variety of an *Anigozanthos* hybrid ornamental plant known as 'Ramboramp'. Plant observations were made on plants grown in Tuggerah, New South Wales, Australia. Unless indicated otherwise, the descriptions disclosed herein are based upon observations made from January 2008 of mature 'Ramboramp' plants grown in nursery pots in greenhouse and outdoor growing areas with day temperature ranging from 25° C. to 27° C., night temperatures ranging from 6° C. to 8° C., and light levels ranging from 6 to 8 klux. Plants were grown for about 24 weeks with one plant per 14 cm container. Those skilled in the art will appreciate that certain characteristics will vary with older or, conversely, younger plants. 'Ramboramp' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 2007 edition.

Botanical classification: *Anigozanthos* hybrid cultivar Ramboramp.

Parentage:

*Parents.*—Unnamed *Anigozanthos* hybrid.

Propagation:

*Type.*—In vitro propagation of micro-plants.

*Time to initiate roots, summer.*—About 7 to 10 days at temperatures of 25° C.

*Time to initiate roots, winter.*—About two weeks at temperatures of 15° C.

*Time to produce a rooted young plant, summer.*—About 45 to 60 days at temperatures of 25° C.

*Time to produce a rooted young plant, winter.*—About 55 to 70 days at temperatures of 15° C.

*Root description.*—Fibrous, freely branching, and white in color.

*Rooting habit.*—Freely branching.

Plant description:

*Plant and growth habit.*—Inverted triangle; compact, upright and outwardly spreading plant habit with branched flowering stems with predominately orange-red colored flowers. Vigorous growth habit.

*Plant height.*—Average plant height including the inflorescence is about 95 cm (range 85 to 105 cm). Average height of foliage is 40 cm (range 30 to 45 cm).

*Plant diameter.*—Average plant spread of a mature plant grown in 20 cm nursery pots or field plots in Sydney, New South Wales, Australia is 40 cm (observed summer 2007 through 2008).

*Lateral branch.*—Quantity per plant: About 30. Strength: Strong. Diameter: About 2.0 cm. Length of central internode: Approximately 3.0 mm. Texture: Smooth, glabrous. Color: 145B.

Foliage description:

*General description.*—The leaf attitude is erect to semi-erect and the degree of leaf curvature is slightly curved. Arrangement: Alternate equitant, simple; sessile.

*Leaves.*—Length: About 35 cm to 40 cm in a 30 cm pot. Width: About 1.6 cm to 1.8 cm in a 30 cm pot. Shape: Linear-slightly falcate. Apex: Acute. Base: Cauline. Margin: Entire. Texture, upper and lower surfaces: Smooth, glabrous; very weak glaucosity and sparsely pubescent on leaf margin. Venation pattern: Parallel. Color of the upper and lower surfaces: 147A with indistinguishable venation (observed summer 2007 through 2008).

Flower description:

*General description.*—Flowers arranged singly on terminal and axillary racemes. Flowers with tubular perianth; zygomorphic. Terminal flowers are held upright and attitude of flowers gradually changes to a horizontal position proximally. The proximal flowers are the first to open and usually are the only flowers to express perianth lobe reflexure. Flowers not fragrant. Flowers persistent. The length of the lowest inflorescence branch including raceme: About 17 cm to 20 cm. Number of flowers per inflorescence: About 3 racemes per inflorescence, each with about 18 to 25 flowers greater in length than 3.0 mm in a 30 cm pot (observed summer 2007 through 2008). Inflorescence height: About 95 cm. Inflorescence diameter: About 20 cm to 25 cm. Flower diameter: About 8.0 mm to 9.0 mm behind the lobes and about 2.6 cm across the lobes on an opened flower. Flower height: About 9.0 mm behind the lobes and about 1.5 cm across the lobes on an opened flower.

*Natural flowering season.*—'Ramboramp' flowers continuously from early spring to winter under outdoor growing conditions in Sydney, New South Wales, Australia.

*Bud just before opening.*—Shape: Tubular. Length: About 4.5 cm. Width: About 6.0 mm. Texture: Tomentose. Color: 144A with dense pubescence colored 59B to 59C.

*Perianth.*—Arrangement: Fused elongated tube with six weakly reflexed acute lobes; split on lower surface. Appearance: Flared distally. Perianth tube length: About 4.0 cm to 4.5 cm. Perianth tube diameter: About 9.0 mm. Lobe length: About 1.5 cm. Lobe width: About 5 mm at base. Texture, outer surface of perianth tube: Tomentose. Texture, inner surface of perianth tube: Smooth, glabrous. Color: When opening and fully opened, outer surface of perianth tube: hairs predominantly 59B to 59C with some NN155B. When opening and fully opened, inner surface of perianth tube: 144B. The combination of these hair colors over the inner surface color of the perianth tube creates an overall orange red effect.

*Floral bracts.*—Length: Up to 10 cm. Width: About 8.0 mm at base. Shape: Ensiform tapering to a narrow conduplicate form at the apex. Apex: narrow acute. Base: Clasping. Margin: Entire. Texture, upper surface: Smooth, glabrous. Texture, lower surface: Tomentose. Color, upper surface: 137B. Color, lower surface: 137B.

*Peduncle* (*flowering stems*).—Strength: Strong, stout. Aspect: Upright to outwardly spreading. Length: About 90 cm to 95 cm. Diameter at base: About 9.0 mm. Texture: Tomentose. Color of surface: 146B with pubescence color ranging from 59A through 59B or NN155B.

*Pedicels* (*individual flower stems*).—Length: About 4 mm. Diameter: About 2 mm. Angle: Distally appressed to flowering stems, then about 30° to 45° from flowering stems proximally with the largest, most mature flowers. Strength: Strong. Texture: Tomentose. Color: 144A with pubescence color NN155B with tips of some hairs colored ranging from 59C through 59D.

*Reproductive organs.*—Stamens: Quantity: 6 per flower with 4 anthers at top of perianth. Anther shape: Oblong. Anther size: About 1 mm by 3 mm. Anther color: 12B. Pollen amount: Scarce. Pollen color: 12B. Pistils: Quantity: One per flower. Pistil length: About 4.5 cm. The position of the stigma in relation to the anthers is level. Style length: About 3.8 cm. Style color: 145A. Stigma shape: Rounded. Stigma color: 144A. Ovary color: 144A with prominent pubescence 59B to 59C creating a darker ovary coloration compared to the perianth tube.

Seed and fruit production: Seed and fruit development have not been observed on plants of the new *Anigozanthos*.

Environmental tolerances: 'Ramboramp' plants have exhibited good tolerance to rain and wind and to tolerate temperatures from 1° C. to about 40° C. 'Ramboramp' has moderate to good drought tolerance. 'Ramboramp' has moderate to good recovery with watering after severe wilting. 'Ramboramp' does well in sandy and gravelly soils.

Disease resistance: 'Ramboramp' has been observed have good tolerance to typical diseases of *Anigozanthos* including Alternaria, Crown Rot and Rust diseases.

What is claimed is:

1. A new and distinct variety of *Anigozanthos* hybrid plant named 'Ramboramp', substantially as herein shown and described.

* * * * *